(12) United States Patent
Chia et al.

(10) Patent No.: US 9,034,352 B2
(45) Date of Patent: May 19, 2015

(54) MICROBICIDE COMBINATIONS CONTAINING SILVER

(75) Inventors: Li-Liang Shen Chia, Ambler, PA (US); Terry Michael Williams, Lower Gwynedd, PA (US)

(73) Assignee: Rohm and Haas Company, Philadelphia, PA (US)

( * ) Notice: Subject to any disclaimer, the term of this patent is extended or adjusted under 35 U.S.C. 154(b) by 696 days.

(21) Appl. No.: 11/978,433

(22) Filed: Oct. 29, 2007

(65) Prior Publication Data

US 2008/0112920 A1  May 15, 2008

Related U.S. Application Data

(60) Provisional application No. 60/858,848, filed on Nov. 14, 2006.

(51) Int. Cl.
| | | |
|---|---|---|
| *A01N 55/02* | (2006.01) | |
| *A01P 1/00* | (2006.01) | |
| *A01N 25/10* | (2006.01) | |
| *A01N 59/16* | (2006.01) | |

(52) U.S. Cl.
CPC ............... *A01N 25/10* (2013.01); *A01N 59/16* (2013.01)

(58) Field of Classification Search
CPC ...................................................... A01N 59/00
See application file for complete search history.

(56) References Cited

U.S. PATENT DOCUMENTS

| 4,542,169 | A | * | 9/1985 | Costerton | ...................... 523/121 |
|---|---|---|---|---|---|
| 5,154,920 | A | * | 10/1992 | Flesher et al. | ................. 514/643 |
| 5,736,591 | A | | 4/1998 | Dunn | |
| 5,849,311 | A | | 12/1998 | Sawan et al. | |
| 6,224,579 | B1 | | 5/2001 | Modak et al. | |
| 2003/0044447 | A1 | | 3/2003 | Zanini et al. | |
| 2005/0049224 | A1 | * | 3/2005 | Gaglani et al. | ................... 514/58 |
| 2005/0058689 | A1 | * | 3/2005 | McDaniel | ..................... 424/426 |
| 2005/0124724 | A1 | | 6/2005 | Burton et al. | |
| 2005/0227895 | A1 | * | 10/2005 | Ghosh et al. | .................. 510/383 |
| 2006/0009553 | A1 | | 1/2006 | Sin | |

FOREIGN PATENT DOCUMENTS

| EP | 1190622 A | 3/2002 |
|---|---|---|
| EP | 1584235 A | 10/2005 |
| JP | H11-222402 | 8/1999 |

* cited by examiner

*Primary Examiner* — Kyle Purdy
(74) *Attorney, Agent, or Firm* — Kenneth Crimaldi

(57) ABSTRACT

A synergistic microbicidal composition. The composition comprises a silver-containing copolymer comprising polymerized units of a monomer X and a monomer Y; wherein monomer X is an ethylenically unsaturated compound having a substituent group selected from an unsaturated or aromatic heterocyclic group having at least one hetero atom selected from N, O and S; wherein monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof; and at least one organic biocide.

7 Claims, No Drawings ional Patent Application No. 60/858,848 filed on Nov. 14, 2006.

MICROBICIDE COMBINATIONS CONTAINING SILVER

This application claims the benefit of priority under 35 U.S.C. §119(e) of U.S. Provisional Patent Application No. 60/858,848 filed on Nov. 14, 2006.

The present invention relates to microbicide combinations containing silver, and in particular to combinations of organic biocides with polymers complexed with silver ion.

A silver-containing copolymer having monomer units derived from vinylpyridine is disclosed in Japanese Kokai H11-222402. However, this reference does not teach combinations of this copolymer with other biocidal agents.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. The problem addressed by this invention is to provide such synergistic combinations of antimicrobial compounds.

The present invention is directed to a synergistic microbicidal composition. The composition comprises: (a) a silver-containing copolymer comprising polymerized units of a monomer X and a monomer Y; wherein monomer X is an ethylenically unsaturated compound having a substituent group selected from an unsaturated or aromatic heterocyclic group having at least one hetero atom selected from N, O and S; alternatively the substituent group is selected from an unsaturated or aromatic heterocyclic group having at least one hetero N atom; and wherein monomer Y is an ethylenically unsaturated compound selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof; and (b) 4,5-dichloro-2-n-octyl-4-isothiazolin-3-one, 2-n-octyl-4-isothiazolin-3-one, 5-chloro-2-methyl-4-isothiazolin-3-one, 2-methyl-4-isothiazolin-3-one, $C_{12}$-$C_{16}$ alkyl dimethylbenzylammonium chloride, diisobutylphenoxyethoxyethyl dimethylbenzylammonium chloride, $C_9$-$C_{15}$ alkyltolylmethy trimethylammonium chloride, benzisothiazolin-3-one, hydrogen peroxide, sodium hypochlorite, glutaraldehyde, 5-chloro-2-(2,4-dichlorophenoxy)phenol, 3-iodo-2-propynylbutyl carbamate or a combination thereof.

The term "copolymer" as used herein and in the appended claims refers to polymers polymerized from at least two different monomers. Percentages herein are by weight, unless specified otherwise. Monomer unit percentages are based on total copolymer weight.

The term "aqueous" as used herein and in the appended claims means water and mixtures composed substantially of water and water miscible solvents.

The use of the term "(meth)" followed by another term such as acrylic, acrylate, acrylamide, etc., as used herein and in the appended claims, refers to, for example, both acrylic and methacrylic; acrylate and methacrylate; acrylamide and methacrylamide; etc.

The glass transition temperature ("Tg") for the copolymers and pressure sensitive adhesive formulations of the present invention may be measured by differential scanning calorimetry (DSC) taking the mid-point in the heat flow versus temperature transition as the Tg value.

In some embodiments of the present invention, the copolymer comprises at least 15 wt % of monomer X derived units. In some aspects of these embodiments, the copolymer comprises at least 20 wt % of monomer X derived units. In some aspects of these embodiments, the copolymer comprises at least 25 wt % of monomer X derived units. In some aspects of these embodiments, the copolymer comprises at least 30 wt % of monomer X derived units. In some aspects of these embodiments, the copolymer comprises at least 35 wt % of monomer X derived units, alternatively at least 40 wt %. In some aspects of these embodiments, the copolymer comprises no more than 60 wt % of monomer X derived units, alternatively no more than 55 wt %, alternatively no more than 50 wt %.

In some embodiments of the present invention, monomer X is selected from vinylimidazoles, vinylimidazolines, vinylpyridines, vinylpyrroles, derivatives thereof and combinations thereof. In some aspects of these embodiments, monomer X is selected from vinylimidazoles, vinylpyridines, derivatives thereof and combinations thereof. In some aspects of these embodiments, monomer X is selected from N-vinylimidazole, 2-vinylpyridine, 4-vinylpyridine and combinations thereof. In some aspects of these embodiments, monomer X is N-vinylimidazole (VI).

In some embodiments of the present invention, monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof. In some aspects of these embodiments, monomer Y is selected from carboxylic acids, carboxylic acid esters (e.g., alkyl (meth)acrylates), (meth)acrylamides, $C_8$-$C_{20}$ aromatic monomers containing at least one exocyclic ethylenic unsaturation and combinations thereof. In some aspects of these embodiments, monomer Y is selected from acrylic acid (AA), methacrylic acid, itaconic acid, maleic acid, fumaric acid, methyl (meth)acrylate, ethyl (meth)acrylate, propyl (meth)acrylate, isopropyl acrylate, n-butyl (meth)acrylate, isobutyl (meth)acrylate, 2-ethylhexyl (meth)acrylate, decyl (meth)acrylate, lauryl (meth)acrylate, stearyl (meth)acrylate, styrene, vinyltoluene, α-methylstyrene and combinations thereof. In some aspects of these embodiments, monomer Y comprises at least one $C_2$-$C_8$ alkyl (meth)acrylate, alternatively n-butyl (meth)acrylate, alternatively monomer Y comprises n-butyl acrylate (BA) and acrylic acid.

In some embodiments of the present invention, the method uses a copolymer comprising polymerized units of a monomer X and a monomer Y; wherein the copolymer comprises at least 15 wt % of monomer X derived units; wherein monomer X is selected from vinylimidazoles, vinylimidazolines, vinylpyridines, vinylpyrroles, derivatives thereof and combinations thereof; and wherein monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof; and with the proviso that the composition comprises no more than 5 wt % of units derived from ethylenically unsaturated monomer containing an epoxide function. In some aspects of these embodiments, the copolymer comprises no more than 1 wt % of units derived from ethylenically unsaturated monomer containing an epoxide function. In some aspects of these embodiments, the copolymer comprises no more than 0.5 wt % of units derived from ethylenically unsaturated monomer containing an epoxide function. In some aspects of these embodiments, the copolymer comprises no more than 0.1 wt % of units derived from ethylenically unsaturated monomer containing an epoxide function. In some aspects of these embodiments, the copolymer comprises no more than 0.05 wt % of units derived from ethylenically unsaturated monomer containing an epoxide function.

In some embodiments of the present invention, the composition comprising a copolymer has a pH of at least 7. In some aspects of these embodiments, the composition has a pH of 7-10. In some aspects of these embodiments, the composition has a pH of at least 8. In some aspects of these embodiments, the composition has a pH of 8-10. In some aspects of these embodiments, the composition has a pH of at least 9. In some aspects of these embodiments, the composition has a pH of 9-10.

In some embodiments of the present invention, the composition comprising a copolymer comprises at least 20 wt % solids. In some aspects of these embodiments, the composition comprises at least 25 wt % solids. In some aspects of these embodiments, the composition comprises at least 30 wt % solids.

In some embodiments of the present invention, the composition comprises from 35 to 55 wt % of polymerized units derived from monomer X and 45 to 65 wt % of polymerized units derived from monomer Y. In some aspects of these embodiments, the composition comprises from 40 to 50 wt % of polymerized units derived from monomer X and 50 to 60 wt % of polymerized units derived from monomer Y.

In some embodiments of the present invention, the composition comprises polymerized units derived from a crosslinker. Crosslinkers suitable for use with the present invention include multi-ethylenically unsaturated monomers. In some aspects of these embodiments, the crosslinker derived units are derived from crosslinker selected from 1,4-butanediol diacrylate; 1,4-butanediol dimethacrylate; 1,6-hexanediol diacrylate; 1,1,1-trimethylol propane triacrylate; 1,1,1-trimethylol propane trimethacrylate; allyl methacrylate; divinylbenzene; and N-allyl acrylamide. In some aspects of these embodiments, the crosslinker derived units are derived from crosslinker selected from 1,1,1-trimethylol propane trimethacrylate. In some aspects of these embodiments, the composition comprises 0.01 to 10 wt % (based on solids) crosslinker. In some aspects of these embodiments, the composition comprises 0.01 to 5 wt % (based on solids) crosslinker. In some aspects of these embodiments, the composition comprises 0.01 to 1 wt % (based on solids) crosslinker.

In one embodiment of the invention, the copolymer comprises from 1.5 wt % to 20 wt % silver based on total weight of copolymer and silver, alternatively from 2.5 wt % to 15 wt %, alternatively from 5 wt % to 11.5 wt %, alternatively from 6.5 wt % to 8.5 wt %. Silver is in the form of Ag(I) ion, which typically is introduced in the form of silver nitrate. Methods for preparation of the copolymer have been disclosed previously, e.g., in U.S. Pat. Appl. Pub. No. US 2005/0227895.

In one embodiment of the invention, the antimicrobial composition comprises a silver-containing copolymer; and 4,5-dichloro-2-n-octyl-4-isothiazolin-3-one (DCOIT). Preferably, a weight ratio of silver to DCOIT is from 1:0.014 to 1:20, more preferably from 1:0.014 to 1:15.

In one embodiment of the invention, the antimicrobial composition comprises a silver-containing copolymer; and 2-n-octyl-4-isothiazolin-3-one (OIT). Preferably, a weight ratio of silver to OIT is from 1:0.039 to 1:8360.

In one embodiment of the invention, the antimicrobial composition comprises a silver-containing copolymer; and a 3:1 mixture of 5-chloro-2-methyl-4-isothiazolin-3-one (CMIT) and 2-methyl-4-isothiazolin-3-one (MIT). Preferably, a weight ratio of silver to the CMIT/MIT mixture is from 1:0.039 to 1:140.

In one embodiment of the invention, the antimicrobial composition comprises a silver-containing copolymer; and MIT. Preferably, a weight ratio of silver to MIT is from 1:39.2 to 1:3020.

In one embodiment of the invention, the antimicrobial composition comprises a silver-containing copolymer; and $C_{12}$-$C_{16}$ alkyl dimethylbenzylammonium chloride. Preferably, a weight ratio of silver to $C_{12}$-$C_{16}$ alkyl dimethylbenzylammonium chloride is from 1:7.76 to 1:1000, more preferably from 1:32 to 1:980.

In one embodiment of the invention, the antimicrobial composition comprises a silver-containing copolymer; and diisobutylphenoxyethoxyethyl dimethylbenzylammonium chloride. Preferably, a weight ratio of silver to diisobutylphenoxyethoxyethyl dimethylbenzylammonium chloride is from 1:1.94 to 1:576.

In one embodiment of the invention, the antimicrobial composition comprises a silver-containing copolymer; and $C_9$-$C_{15}$ alkyltolylmethyltrimethylammonium chloride. Preferably, a weight ratio of silver to $C_9$-$C_{15}$ alkyltolylmethyltrimethylammonium chloride is from 1:26 to 1:6040.

In one embodiment of the invention, the antimicrobial composition comprises benzisothiazolin-3-one and a silver-containing copolymer. Preferably, a weight ratio of benzisothiazolin-3-one to silver is from 1:0.0002 to 1:1.

In one embodiment of the invention, the antimicrobial composition comprises hydrogen peroxide and a silver-containing copolymer. Preferably, a weight ratio of hydrogen peroxide to silver is from 1:0.000005 to 1:0.01.

In one embodiment of the invention, the antimicrobial composition comprises sodium hypochlorite and a silver-containing copolymer. Preferably, a weight ratio of sodium hypochlorite to silver is from 1:0.008 to 1:200.

In one embodiment of the invention, the antimicrobial composition comprises glutaraldehyde and a silver-containing copolymer. Preferably, a weight ratio of glutaraldehyde to silver is from 1:0.00006 to 1:0.047.

In one embodiment of the invention, the antimicrobial composition comprises 5-chloro-2-(2,4-dichlorophenoxy)phenol and a silver-containing copolymer. Preferably, a weight ratio of 5-chloro-2-(2,4-dichlorophenoxy)phenol to silver is from 1:0.00011 to 1:0.57.

In one embodiment of the invention, the antimicrobial composition comprises 3-iodo-2-propynylbutyl carbamate and a silver-containing copolymer. Preferably, a weight ratio of 3-iodo-2-propynylbutyl carbamate to silver is from 1:0.000002 to 1:80.

The specific amount of the composition of this invention necessary to inhibit or control the growth of microorganisms in an application will vary. Typically, the amount of the composition of the present invention is sufficient to control the growth of microorganisms if it provides from 0.1 to 25,000 ppm (parts per million) active ingredient of the composition (as silver plus co-biocide combined). It is preferred that the active ingredients of the composition be present in the locus in an amount of at least 0.1 ppm, more preferably at least 5 ppm, more preferably at least 50 ppm and most preferably at least 500 ppm. In one embodiment of the invention, the active ingredients are present in an amount of at least 2,000 ppm. It is preferred that the active ingredients of the composition be present in the locus in an amount of no more than 20,000 ppm, more preferably no more than 15,000 ppm, more, preferably no more than 5,000 ppm. In one embodiment of the invention, the active ingredients are present in an amount of no more than 15,000 ppm, more preferably no more than 8,000 ppm, and most preferably no more than 3,000 ppm.

Some embodiments of the present invention will now be described in detail in the following Examples. The silver-containing copolymer tested in these Examples comprises a polymer having 45% BA monomer units, 45% VI monomer units and 10% AA monomer units, based on polymer weight, and containing 7.8% silver ion, based on total weight of polymer and silver. The silver-containing polymer was formulated in water at 39% solids and pH 11.

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula: $C_a/C_A + C_b/C_B$ = Synergy Index ("SI") wherein:

$C_A$ = concentration of compound A (first component) in ppm, acting alone, which produced an end point (MIC of Compound A).

$C_a$ = concentration of compound A in ppm, in the mixture, which produced an end point.

$C_B$ = concentration of compound B (second component) in ppm, acting alone, which produced an end point (MIC of Compound B).

$C_b$ = concentration of compound B in ppm, in the mixture, which produced an end point.

When the sum of $C_a/C_A$ and $C_b/C_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of an antimicrobial compound is the lowest concentration tested under a specific set of conditions that prevents the growth of added microorganisms.

Synergy tests were conducted using standard microtiter plate assays with media designed for optimal growth of the test microorganism. Soybean Casein Digest Broth (Tryptic Soy Broth, TSB medium) or minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of the biocides. High resolution MICs were determined by adding varying amounts of microbicide to one column of a microtitre plate and doing subsequent ten-fold dilutions using an automated liquid handling system.

The synergy of the combinations of the present invention was determined against four bacteria, gram positive *Staphylococcus aureus* (*S. aureus*—ATCC #6538) and gram negative *Pseudomonas aeruginosa* (*P. aeruginosa*—ATCC #15442), *Samonella choleraesuis* (*S. choleraesuis*—ATCC #10708) and *Escherichia coli* (*E. coli*—ATCC #8739), a yeast, *Candida albicans* (*C. albicans*—ATCC 10231), and a mold, *Aspergillus niger* (*A. niger*—ATCC 16404). The bacteria were used at a concentration of about $1-6\times10^6$ bacteria per mL and the yeast and mold at $1-5\times10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the microbicide combinations of the present invention are shown below in the Tables. Each table shows the specific combinations of component (a) and the second component (b); results against the microorganisms tested with incubation times; the endpoint activity in ppm measured by the MIC for Component (a) ($C_a$), for the second component alone ($C_b$), for the mixture ($C_a$) and for second component in the mixture ($C_b$); the calculated SI value; and the range of synergistic ratios for each combination tested (first component/second component or a+b). The end point values in the following examples for the silver-polymer complex are reported on an active silver ion basis.

TABLE 1

| Test Organisms | Contact Time | Ca | Cb | S.I. | Ca:Cb |
|---|---|---|---|---|---|
| S. choleraesuis ATCC # 10708 | 24 hour | 0.1 | — | — | |
| | | — | 0.3 | — | |
| | | 0.01 | 0.2 | 0.77 | 1:20 |
| | | 0.025 | 0.2 | 0.92 | 1:8 |
| S. aureus ATCC # 6538) | 24 hour | 0.5 | — | — | |
| | | — | 0.99 | — | |
| | | 0.01 | 0.81 | 0.84 | 1:81 |
| | | 0.025 | 0.58 | 0.64 | 1:23.2 |
| | | 0.1 | 0.58 | 0.79 | 1:5.8 |
| | | 0.15 | 0.2 | 0.5 | 1:1.33 |
| | | 0.25 | 0.16 | 0.66 | 1:0.64 |
| | 48 hour | 0.5 | — | — | |
| | | — | 0.99 | — | |
| | | 0.01 | 1 | 0.73 | 1:100 |
| | | 0.025 | 0.8 | 0.62 | 1:32 |
| | | 0.1 | 0.58 | 0.61 | 1:5.8 |
| | | 0.15 | 0.2 | 0.44 | 1:1.33 |
| | | 0.25 | 0.16 | 0.61 | 1:0.64 |
| E. coli ATCC # 8739 | 24 hour | 0.25 | — | — | |
| | | — | 1.2 | — | |
| | | 0.01 | 1 | 0.87 | 1:100 |
| | | 0.05 | 0.8 | 0.87 | 1:16 |
| | | 0.1 | 0.8 | 1.07 | 1:8 |
| | | 0.15 | 0.16 | 0.73 | 1:1.07 |
| | 48 hour | 0.25 | — | — | |
| | | — | 1.6 | — | |
| | | 0.01 | 1.4 | 0.92 | 1:140 |
| | | 0.025 | 1.4 | 0.98 | 1:56 |
| | | 0.15 | 0.2 | 0.73 | 1:1.33 |
| C. albicans ATCC # 10231 | 24 hour | 5 | — | — | |
| | | — | 1.6 | — | |
| | | 2.5 | 1.9 | 1.01 | 1:0.76 |
| | 48 hour | 10 | — | — | |
| | | — | 3.9 | — | |
| | | 2.5 | 1.6 | 0.66 | 1:0.64 |
| | | 5 | 1.6 | 0.91 | 1:0.32 |
| A. niger ATCC # 16404 | 3 days | 5 | — | — | |
| | | — | 3.9 | — | |
| | | 2.5 | 1.96 | 1.01 | 1:0.78 |
| | 7 days | 20 | — | — | |
| | | — | 3.9 | — | |
| | | 5 | 1.21 | 0.56 | 1:0.24 |
| | | 10 | 0.99 | 0.76 | 1:0.1 |
| | | 15 | 0.58 | 0.9 | 1:0.039 |

Ca = Component A (Ag-polymer formulation)
Cb = Component B (CMIT/MIT)

TABLE 2

| Test Organisms | Contact Time | Ca | Cb | S.I. | Ca:Cb |
|---|---|---|---|---|---|
| P. aeruginosa ATCC # 15442 | 24 hour | 0.1 | — | — | |
| | | — | 443.5 | — | |
| | | 0.025 | 361 | 1.06 | 1:14440 |

TABLE 2-continued

| Test Organisms | Contact Time | Ca | Cb | S.I. | Ca:Cb |
|---|---|---|---|---|---|
| S. choleraesuis ATCC # 10708 | 24 hour | 0.1 | — | | |
| | | — | 361 | | |
| | | 0.05 | 209 | 1.08 | 1:4180 |
| | 48 hour | 0.1 | — | | |
| | | — | 361 | | |
| | | 0.05 | 209 | 1.08 | 1:4180 |
| S. aureus ATCC # 6538 | 24 hour | 0.5 | — | | |
| | | — | 72.8 | — | |
| | | 0.025 | 58.8 | 0.86 | 1:2352 |
| | | 0.1 | 58.8 | 1.01 | 1:588 |
| | | 0.15 | 50.8 | 1 | 1:338.7 |
| | 48 hour | 0.5 | — | | |
| | | — | 72.8 | — | |
| | | 0.01 | 72.8 | 1.02 | 1:7280 |
| | | 0.025 | 72.8 | 1.05 | 1:2912 |
| E. coli ATCC # 9739 | 24 hour | 0.25 | — | | |
| | | — | 294 | — | |
| | | 0.01 | 294 | 1.04 | 1:29400 |
| | | 0.025 | 209 | 0.81 | 1:8360 |
| | | 0.05 | 209 | 0.91 | 1:4180 |
| | | 0.1 | 141 | 0.88 | 1:1410 |
| | | 0.15 | 141 | 1.08 | 1:940 |
| | 48 hour | 0.25 | — | — | |
| | | — | 294 | — | |
| | | 0.01 | 294 | 1.04 | 1:29400 |
| | | 0.05 | 209 | 0.91 | 1:4180 |
| C. albicans ATCC # 10231 | 24 hour | 5 | — | — | |
| | | — | 0.81 | — | |
| | | 2.5 | 0.39 | 0.98 | 1:0.156 |
| | | 2.5 | 0.2 | 0.75 | 1:0.08 |
| | | 2.5 | 0.16 | 0.70 | 1:0.064 |
| | 48 hour | 0.25 | — | — | |
| | | — | 0.99 | — | |
| | | 2.5 | 0.58 | 0.84 | 1:0.232 |
| | | 2.5 | 0.39 | 0.64 | 1:0.156 |
| A. niger ATCC # 16404 | 3 days | 5 | — | — | |
| | | — | 3.9 | — | |
| | | 2.5 | 1.59 | 0.91 | 1:0.636 |
| | | 2.5 | 1.38 | 0.86 | 1:0.552 |
| | 7 days | 20 | — | | |
| | | — | 5.76 | — | |
| | | 2.5 | 1.96 | 0.47 | 1:0.784 |
| | | 5 | 1.21 | 0.46 | 1:0.242 |
| | | 10 | 0.99 | 0.67 | 1:0.1 |
| | | 15 | 0.58 | 0.85 | 1:0.039 |

Ca = Component A (Ag-polymer formulation)
Cb = Component B (OIT)

TABLE 3

| Test-Organisms | Contact Time | Ca | Cb | S.I. | Ca:Cb |
|---|---|---|---|---|---|
| P. aerginosa ATCC # 15442 | 48 hour | 0.1 | — | | |
| | | — | 24.7 | | |
| | | 0.01 | 20.2 | 0.92 | 1:2020 |
| | | 0.025 | 20.2 | 1.07 | 1:808 |
| S. aureus ATCC # 6538 | 24 hour | 0.5 | — | — | |
| | | — | 34.5 | — | |
| | | 0.01 | 30.2 | 0.9 | 1:3020 |
| | | 0.025 | 30.2 | 0.93 | 1:1208 |
| | | 0.1 | 24.7 | 0.92 | 1:247 |
| | | 0.15 | 24.7 | 1.02 | 1:164.67 |
| | | 0.25 | 14.4 | 0.92 | 1:57.6 |
| | 48 hour | 0.5 | — | — | |
| | | — | 34.5 | — | |
| | | 0.01 | 34.5 | 1.02 | 1:3450 |
| | | 0.025 | 34.5 | 1.05 | 1:1380 |
| | | 0.1 | 30.2 | 1.08 | 1:302 |
| | | 0.25 | 14.4 | 0.92 | 1:57.6 |
| C. albicans ATCC # 10231 | 24 hour | 5 | — | — | |
| | | — | 288 | — | |
| | | 2.5 | 98 | 0.84 | 1:39.2 |
| | 48 hour | 10 | — | — | |
| | | — | 403 | — | |
| | | 2.5 | 288 | 0.96 | 1:115.2 |
| | | 5 | 194 | 0.98 | 1:38.8 |
| A. niger ATCC # 16404 | 3 days | 5 | — | — | |
| | | — | 493 | — | |
| | | 2.5 | 288 | 1.08 | 1:115.2 |
| | 7 days | 20 | — | — | |
| | | — | 603 | — | |
| | | 5 | 493 | 1.07 | 1:98.6 |
| | | 10 | 288 | 0.98 | 1:28.8 |
| | | 15 | 98 | 0.91 | 1:6.53 |

Ca = Component A (Ag-polymer formulation)
Cb = Component B (MIT)

TABLE 4

| Test Organisms | Contact Time | Ca | Cb | S.I. | Ca:Cb |
|---|---|---|---|---|---|
| P. aerginosa ATCC # 15442 | 24 hour | 0.1 | — | — | |
| | | — | 1.5 | — | |
| | | 0.01 | 1.47 | 1.08 | 1:147 |
| | 48 hour | 0.1 | — | — | |
| | | — | 2.9 | — | |
| | | 0.05 | 0.29 | 0.91 | 1:5.8 |
| S. choleraesuis ATCC # 10708 | 248 hour | 0.1 | — | — | |
| | | — | 1.5 | — | |
| | | 0.05 | 0.29 | 0.69 | 1:5.8 |
| S. aureus ATCC # 6538 | 24 hour | 0.5 | — | — | |
| | | — | 0.29 | — | |
| | | 0.01 | 0.1 | 0.36 | 1:10 |
| | | 0.025 | 0.1 | 0.39 | 1:4 |
| | | 0.05 | 0.1 | 0.44 | 1:2 |
| | | 0.1 | 0.07 | 0.44 | 1:0.7 |
| | | 0.15 | 0.04 | 0.44 | 1:0.27 |
| | | 0.25 | 0.04 | 0.64 | 1:0.16 |
| | 48 hour | 0.5 | — | — | |
| | | — | 0.29 | — | |
| | | 0.01 | 0.15 | 0.54 | 1:15 |
| | | 0.025 | 0.15 | 0.57 | 1:6 |
| | | 0.05 | 0.15 | 0.62 | 1:3 |
| | | 0.1 | 0.07 | 0.44 | 1:0.7 |
| | | 0.15 | 0.06 | 0.51 | 1:0.4 |
| | | 0.25 | 0.06 | 0.71 | 1:0.24 |
| E. coli ATCC # 9739 | 24 hour | 0.25 | — | — | |
| | | — | 0.29 | — | |
| | | 0.01 | 0.1 | 0.38 | 1:10 |
| | | 0.025 | 0.07 | 0.34 | 1:2.8 |
| | | 0.05 | 0.07 | 0.44 | 1:1.4 |
| | | 0.1 | 0.06 | 0.61 | 1:0.6 |
| | | 0.15 | 0.04 | 0.74 | 1:0.27 |
| | 48 hour | 0.25 | — | — | |
| | | — | 0.43 | — | |
| | | 0.01 | 0.1 | 0.27 | 1:10 |
| | | 0.025 | 0.1 | 0.33 | 1:4 |
| | | 0.05 | 0.07 | 0.36 | 1:1.4 |
| | | 0.1 | 0.06 | 0.54 | 1:0.6 |
| | | 0.15 | 0.06 | 0.74 | 1:0.4 |
| C. albicans ATCC # 10231 | 48 hour | 10 | — | — | |
| | | — | 0.15 | — | |
| | | 2.5 | 0.07 | 0.72 | 1:0.028 |
| | | 5 | 0.07 | 0.97 | 1:0.014 |
| A. niger ATCC # 16404 | 7 days | 20 | — | — | |
| | | — | 2 | — | |
| | | 2.5 | 1 | 0.63 | 1:0.4 |
| | | 5 | 0.7 | 0.6 | 1:0.14 |
| | | 10 | 0.7 | 0.85 | 1:0.07 |
| | | 15 | 0.48 | 0.99 | 1:0.03 |

Ca = Component A (Ag-polymer formulation)
Cb = Component B (DCOIT)

TABLE 5

| Test Organisms | Contact Time | Ca | Cb | S.I. | Ca:Cb |
|---|---|---|---|---|---|
| S. choleraesuis ATCC # 10708 | 48 hour | 0.1 | — | — | |
| | | — | 6.9 | — | |
| | | 0.01 | 6 | 0.97 | 1:600 |
| S. aureus ATCC # 6538 | 24 hour | 0.5 | — | — | |
| | | — | 19.4 | — | |
| | | 0.01 | 9.8 | 0.53 | 1:980 |
| | | 0.025 | 9.8 | 0.56 | 1:392 |
| | | 0.05 | 4.9 | 0.35 | 1:98 |
| | | 0.1 | 4.9 | 0.45 | 1:49 |
| | | 0.15 | 4.9 | 0.55 | 1:32.67 |
| | | 0.25 | 4.9 | 0.75 | 1:19.6 |
| | 48 hour | 0.5 | — | — | |
| | | — | 19.4 | — | |
| | | 0.01 | 19.4 | 1.02 | 1:1940 |
| | | 0.025 | 19.4 | 1.05 | 1:776 |
| | | 0.05 | 9.8 | 0.61 | 1:196 |
| | | 0.1 | 9.8 | 0.71 | 1:98 |
| | | 0.15 | 8 | 0.71 | 1:53.33 |
| | | 0.25 | 8 | 0.91 | 1:32 |
| E. coli ATCC # 9739 | 48 hour | 0.25 | — | — | |
| | | — | 4.9 | — | |
| | | 0.01 | 4.9 | 1.04 | 1:490 |
| | | 0.025 | 4 | 0.92 | 1:160 |
| | | 0.05 | 4 | 1.02 | 1:80 |
| C. albicans ATCC # 10231 | 24 hour | 5 | — | — | |
| | | — | 40.3 | — | |
| | | 2.5 | 19.4 | 0.98 | 1:7.76 |
| | 48 hour | 10 | — | — | |
| | | — | 98 | — | |
| | | 2.5 | 60.4 | 0.87 | 1:24.16 |
| | | 5 | 49 | 1 | 1:9.8 |
| A. niger ATCC # 16404 | 3 days | 5 | — | — | |
| | | — | 194 | — | |
| | | 2.5 | 80 | 0.91 | 1:32 |
| | 7 days | 20 | — | — | |
| | | — | 603 | — | |
| | | 5 | 194 | 0.92 | 1:38.8 |
| | | 15 | 98 | 1.09 | 1:6.53 |

Ca = Component A (Ag-polymer formulation)
Cb = Component B ($C_{12}$-$C_{16}$ alkyl dimethylbenzylammonium chloride)

TABLE 6

| Test Organisms | Contact Time | Ca | Cb | S.I. | Ca:Cb |
|---|---|---|---|---|---|
| S. aureus ATCC # 6538 | 24 hour | 0.5 | — | — | |
| | | — | 28.8 | — | |
| | | 0.01 | 28.8 | 1.02 | 1:2880 |
| | | 0.025 | 28.8 | 1.05 | 1:1152 |
| | | 0.15 | 28.8 | 0.97 | 1:192 |
| | 48 hour | 0.5 | — | — | |
| | | — | 40.3 | — | |
| | | 0.01 | 40.3 | 1.02 | 1:4030 |
| | | 0.025 | 40.3 | 1.05 | 1:1612 |
| | | 0.05 | 28.8 | 0.81 | 1:576 |
| | | 0.1 | 28.8 | 0.91 | 1:288 |
| | | 0.15 | 28.8 | 1.01 | 1:192 |
| E. coli ATCC # 9739 | 24 hour | 0.25 | — | — | |
| | | — | 19.4 | — | |
| | | 0.01 | 19.4 | 1.04 | 1:1940 |
| | | 0.1 | 9.8 | 0.91 | 1:98 |
| | | 0.15 | 4.9 | 0.85 | 1:32.67 |
| C. albicans ATCC # 10231 | 48 hour | 10 | — | — | |
| | | — | 28.8 | — | |
| | | 2.5 | 19.4 | 0.92 | 1:7.76 |
| A. niger ATCC # 16404 | 7 days | 20 | — | — | |
| | | — | 40.3 | — | |
| | | 5 | 28.8 | 0.96 | 1:5.76 |
| | | 10 | 19.4 | 0.98 | 1:1.94 |

Ca = Component A (Ag-polymer formulation)
Cb = Component B (diisobutylphenoxyethoxyethyl dimethylbenzylammonium chloride)

TABLE 7

| Test Organisms | Contact Time | Ca | Cb | S.I. | Ca:Cb |
|---|---|---|---|---|---|
| P. aeruginosa ATCC # 15442 | 24 hour | 0.1 | — | — | |
| | | — | 19.4 | — | |
| | | 0.025 | 9.8 | 0.76 | 1:392 |
| | | 0.05 | 9.8 | 1.01 | 1:196 |
| | 48 hour | 0.1 | — | — | |
| | | — | 19.4 | — | |
| | | 0.025 | 9.8 | 0.76 | 1:392 |
| | | 0.05 | 9.8 | 1.01 | 1:196 |
| S. aureus ATCC # 6538 | 24 hour | 0.5 | — | — | |
| | | — | 69 | — | |
| | | 0.01 | 60.4 | 0.9 | 1:6040 |
| | | 0.025 | 28.8 | 0.47 | 1:1152 |
| | | 0.05 | 28.8 | 0.52 | 1:576 |
| | | 0.1 | 9.8 | 0.34 | 1:98 |
| | | 0.15 | 9.8 | 0.44 | 1:65.33 |
| | | 0.25 | 9.8 | 0.64 | 1:39.2 |
| | 48 hour | 0.5 | — | — | |
| | | — | 69 | — | |
| | | 0.01 | 69 | 1.02 | 1:6900 |
| | | 0.025 | 28.8 | 0.47 | 1:1152 |
| | | 0.05 | 28.8 | 0.52 | 1:576 |
| | | 0.1 | 19.4 | 0.48 | 1:194 |
| | | 0.15 | 19.4 | 0.58 | 1:129.33 |
| | | 0.25 | 19.4 | 0.78 | 1:77.6 |
| | 48 hour | 4 | — | — | |
| | | — | 44 | — | |
| | | 1 | 26 | 0.84 | 1:26 |
| | | 1 | 33 | 1 | 1:33 |
| | | 2 | 26 | 1.09 | 1:13 |
| E. coli ATCC # 9739 | 24 hour | 0.25 | — | — | |
| | | — | 6 | — | |
| | | 0.01 | 4.9 | 0.86 | 1:490 |
| | | 0.025 | 4 | 0.77 | 1:160 |
| | | 0.05 | 4 | 0.87 | 1:80 |
| | | 0.1 | 4 | 1.07 | 1:40 |
| | 48 hour | 0.25 | — | — | |
| | | — | 6 | — | |
| | | 0.01 | 4.9 | 0.86 | 1:490 |
| | | 0.025 | 4.9 | 0.92 | 1.196 |
| | | 0.05 | 4.9 | 1.02 | 1:98 |
| C. albicans ATCC # 10231 | 24 hour | 5 | — | — | |
| | | — | 98 | — | |
| | | 2.5 | 69 | 0.8 | 1:27.6 |
| A. niger ATCC # 16404 | 7 days | 20 | — | — | |
| | | — | 493 | — | |
| | | 5 | 288 | 0.83 | 1:57.6 |
| | | 10 | 288 | 1.08 | 1:28.8 |

Ca = Component A (Ag-polymer formulation)
Cb = Component B ($C_9$-$C_{15}$ alkyltolylmethyltrimethylammonium chloride)

TABLE 8

| Test Organisms | Contact Time | Ca | Cb | S.I. | Ca:Cb |
|---|---|---|---|---|---|
| P. aeruginosa ATCC # 15442 | 24 hour | 4 | — | — | |
| | | — | 0.06 | — | |
| | | 3 | 0.004 | 0.82 | 1:0.00133 |
| | | 3 | 0.008 | 0.88 | 1:0.00267 |
| | 48 hour | 7 | — | — | |
| | | — | 0.06 | — | |
| | | 5 | 0.001 | 0.73 | 1:0.0002 |
| | | 5 | 0.002 | 0.75 | 1:0.0004 |
| | | 5 | 0.004 | 0.78 | 1:0.0008 |
| | | 5 | 0.008 | 0.85 | 1:0.0016 |
| | | 5 | 0.016 | 0.98 | 1:0.0032 |
| | | 3 | 0.03 | 0.93 | 1:0.01 |
| S. aureus ATCC # 6538) | 24 hour | 20 | — | — | |
| | | — | 0.06 | — | |
| | | 11 | 0.016 | 0.82 | 1:0.00146 |
| | | 9 | 0.016 | 0.72 | 1:0.00178 |
| | | 9 | 0.03 | 0.95 | 1:0.0033 |
| | | 8 | 0.03 | 0.9 | 1:0.00375 |
| | 48 hour | 20 | — | — | |
| | | — | 0.06 | — | |

TABLE 8-continued

| Test Organisms | Contact Time | Ca | Cb | S.I. | Ca:Cb |
|---|---|---|---|---|---|
| | | 11 | 0.01 | 0.72 | 1:0.0009 |
| | | 9 | 0.01 | 0.62 | 1:0.0011 |
| | | 9 | 0.03 | 0.95 | 1:0.0033 |
| C. albicans ATCC # 10231 | 24 hour | 30 | — | — | |
| | | — | 6 | — | |
| | | 20 | 0.5 | 0.75 | 1:0.025 |
| | | 11 | 0.5 | 0.45 | 1:0.0455 |
| | | 20 | 1 | 0.83 | 1:0.05 |
| | | 11 | 1 | 0.53 | 1:0.091 |
| | | 9 | 1 | 0.47 | 1:0.111 |
| | | 11 | 2 | 0.7 | 1:0.182 |
| | | 9 | 2 | 0.63 | 1:0.222 |
| | | 7 | 2 | 0.57 | 1:0.286 |
| | | 9 | 4 | 0.97 | 1:0.444 |
| | | 7 | 4 | 0.9 | 1:0.57 |
| | | 5 | 4 | 0.83 | 1:0.8 |
| | | 4 | 4 | 0.8 | 1:1 |
| | 48 hour | 30 | — | — | |
| | | — | 6 | — | |
| | | 11 | 0.5 | 0.45 | 1:0.0455 |
| | | 20 | 1 | 0.83 | 1:0.05 |
| | | 11 | 1 | 0.53 | 1:0.091 |
| | | 9 | 1 | 0.47 | 1:0.111 |
| | | 10 | 2 | 0.67 | 1:0.2 |
| | | 11 | 2 | 0.7 | 1:0.182 |
| | | 9 | 2 | 0.63 | 1:0.222 |
| | | 7 | 2 | 0.57 | 1:0.286 |
| | | 9 | 4 | 0.97 | 1:0.444 |
| | | 7 | 4 | 0.9 | 1:0.571 |
| | | 5 | 4 | 0.83 | 1:0.8 |
| | | 4 | 4 | 0.8 | 1:1 |
| A. niger ATCC # 16404 | 3 days | 43 | — | — | |
| | | — | 6 | — | |
| | | 30 | 0.5 | 0.78 | 1:0.0167 |
| | | 30 | 1 | 0.86 | 1:0.033 |
| | | 20 | 2 | 0.8 | 1:0.1 |
| | | 11 | 2 | 0.59 | 1:0.182 |
| | | 9 | 2 | 0.54 | 1:0.22 |
| | | 11 | 4 | 0.92 | 1:0.364 |
| | | 9 | 4 | 0.88 | 1:0.444 |
| | | 7 | 4 | 0.83 | 1:0.571 |
| | | 5 | 4 | 0.78 | 1:0.8 |
| | 7 days | 53 | — | — | |
| | | — | 6 | — | |
| | | 43 | 0.5 | 0.89 | 1:0.0116 |
| | | 43 | 1 | 0.98 | 1:0.0233 |
| | | 30 | 2 | 0.9 | 1:0.067 |
| | | 20 | 2 | 0.71 | 1:0.1 |
| | | 11 | 2 | 0.54 | 1:0.182 |
| | | 9 | 2 | 0.5 | 1:0.222 |
| | | 11 | 4 | 0.87 | 1:0.364 |
| | | 9 | 4 | 0.84 | 1:0.444 |
| | | 7 | 4 | 0.8 | 1:0.571 |
| | | 5 | 4 | 0.76 | 1:0.8 |

Ca = Component A - Benzisothiazolin-3-one
Cb = Component B (Ag-polymer formulation)

TABLE 9

| Test Organisms | Contact Time | Ca | Cb | S.I. | Ca:Cb |
|---|---|---|---|---|---|
| P. aeruginosa ATCC # 15442 | 24 hour | 315 | — | — | |
| | | — | 0.06 | — | |
| | | 255 | 0.004 | 0.88 | 1:0.000016 |
| | | 255 | 0.008 | 0.94 | 1:0.000031 |
| | 48 hour | 525 | — | — | |
| | | — | 0.06 | — | |
| | | 390 | 0.002 | 0.78 | 1:0.000005 |
| | | 390 | 0.004 | 0.81 | 1:0.00001 |
| | | 390 | 0.008 | 0.88 | 1:0.000021 |
| | | 315 | 0.016 | 0.87 | 1:0.000051 |
| | | 255 | 0.016 | 0.75 | 1:0.000063 |
| | | 255 | 0.03 | 0.99 | 1:0.000118 |

TABLE 9-continued

| Test Organisms | Contact Time | Ca | Cb | S.I. | Ca:Cb |
|---|---|---|---|---|---|
| S. aureus ATCC # 6538 | 24 hour | 66 | — | — | |
| | | — | 0.06 | — | |
| | | 53 | 0.002 | 0.84 | 1:0.000038 |
| | | 53 | 0.004 | 0.87 | 1:0.000075 |
| | | 53 | 0.008 | 0.94 | 1:0.00015 |
| | | 39 | 0.008 | 0.72 | 1:0.000205 |
| | | 39 | 0.016 | 0.86 | 1:0.00041 |
| | 48 hour | 180 | — | — | |
| | | — | 0.06 | — | |
| | | 120 | 0.002 | 0.7 | 1:0.000017 |
| | | 120 | 0.004 | 0.73 | 1:0.000033 |
| | | 120 | 0.008 | 0.8 | 1:0.000067 |
| | | 66 | 0.008 | 0.5 | 1:0.000121 |
| | | 120 | 0.016 | 0.93 | 1:0.000133 |
| | | 66 | 0.016 | 0.63 | 1:0.000242 |
| | | 66 | 0.03 | 0.87 | 1:0.000455 |
| | | 53 | 0.03 | 0.79 | 1:0.00057 |
| C. albicans ATCC # 10231 | 24 hour | 130 | — | — | |
| | | — | 6 | — | |
| | | 105 | 0.5 | 0.89 | 1:0.00476 |
| | | 105 | 1 | 0.97 | 1:0.0095 |
| | | 85 | 2 | 0.99 | 1:0.0235 |
| | 48 hour | 130 | — | — | |
| | | — | 6 | — | |
| | | 85 | 2 | 0.99 | 1:0.02353 |
| A. niger ATCC # 16404 | 3 days | 1300 | — | — | |
| | | — | 6 | — | |
| | | 1050 | 0.5 | 0.89 | 1:0.00048 |
| | | 1050 | 1 | 0.97 | 1:0.00095 |
| | | 850 | 1 | 0.82 | 1:0.0012 |
| | | 850 | 2 | 0.99 | 1:0.00235 |
| | | 400 | 4 | 0.97 | 1:0.01 |
| | 7 days | 1750 | — | — | |
| | | — | 6 | — | |
| | | 1300 | 0.5 | 0.83 | 1:0.000385 |
| | | 1300 | 1 | 0.91 | 1:0.000769 |
| | | 1050 | 2 | 0.93 | 1:0.001905 |

Ca = Component A (Hydrogen Peroxide)
Cb = Component B (Ag-polymer formulation)

TABLE 10

| Test Organisms | Contact Time | Ca | Cb | S.I. | Ca:Cb |
|---|---|---|---|---|---|
| P. aeruginosa ATCC # 15442 | 24 hour | 0.7 | — | — | — |
| | | — | 0.06 | — | — |
| | | 0.5 | 0.008 | 0.85 | 1:0.016 |
| | | 0.5 | 0.016 | 0.98 | 1:0.032 |
| | 48 hour | 0.9 | — | — | |
| | | — | 0.06 | — | |
| | | 0.7 | 0.008 | 0.91 | 1:0.0114 |
| S. aureus ATCC # 6538 | 24 hour | 0.4 | — | — | |
| | | — | 0.06 | — | |
| | | 0.3 | 0.004 | 0.82 | 1:0.1333 |
| | | 0.2 | 0.004 | 0.57 | 1:0.02 |
| | | 0.3 | 0.008 | 0.88 | 1:0.02 |
| | | 0.2 | 0.008 | 0.63 | 1:0.04 |
| | | 0.2 | 0.016 | 0.77 | 1:0.08 |
| | 48 hour | 0.7 | — | — | |
| | | — | 0.06 | — | |
| | | 0.5 | 0.004 | 0.78 | 1:0.008 |
| | | 0.5 | 0.008 | 0.85 | 1:0.016 |
| | | 0.5 | 0.016 | 0.98 | 1:0.032 |
| C. albicans ATCC # 10231 | 24 hour | 0.9 | — | — | |
| | | — | 6 | — | |
| | | 0.7 | 0.5 | 0.86 | 1:0.714 |
| | | 0.7 | 1 | 0.94 | 1:1.429 |
| | | 0.5 | 1 | 0.72 | 1:2 |
| | | 0.4 | 1 | 0.61 | 1:2.5 |
| | | 0.3 | 1 | 0.5 | 1:3.3 |
| | | 0.2 | 1 | 0.39 | 1:5 |
| | | 0.16 | 1 | 0.34 | 1:6.25 |
| | | 0.09 | 1 | 0.27 | 1:11.1 |

TABLE 10-continued

| Test Organisms | Contact Time | Ca | Cb | S.I. | Ca:Cb |
|---|---|---|---|---|---|
| | | 0.07 | 1 | 0.24 | 1:14.3 |
| | | 0.05 | 1 | 0.22 | 1:20 |
| | | 0.5 | 2 | 0.89 | 1:4 |
| | | 0.4 | 2 | 0.78 | 1:5 |
| | | 0.3 | 2 | 0.67 | 1:6.67 |
| | | 0.2 | 2 | 0.56 | 1:10 |
| | | 0.16 | 2 | 0.51 | 1:12.5 |
| | | 0.09 | 2 | 0.43 | 1:22.2 |
| | | 0.07 | 2 | 0.41 | 1:28.6 |
| | | 0.05 | 2 | 0.39 | 1:40 |
| | | 0.04 | 2 | 0.38 | 1:50 |
| | | 0.2 | 4 | 0.89 | 1:20 |
| | | 0.16 | 4 | 0.84 | 1:25 |
| | | 0.09 | 4 | 0.77 | 1:44.4 |
| | | 0.07 | 4 | 0.74 | 1:57.1 |
| | | 0.05 | 4 | 0.72 | 1:80 |
| | | 0.04 | 4 | 0.71 | 1:100 |
| | | 0.03 | 4 | 0.7 | 1:133.3 |
| | | 0.02 | 4 | 0.69 | 1:200 |
| | 48 hour | 2 | — | — | |
| | | — | 6 | — | |
| | | 1.6 | 0.5 | 0.88 | 1:0.313 |
| | | 0.9 | 0.5 | 0.53 | 1:0.556 |
| | | 1.6 | 1 | 0.97 | 1:0.625 |
| | | 0.9 | 1 | 0.62 | 1:1.11 |
| | | 0.7 | 1 | 0.52 | 1:1.43 |
| | | 0.5 | 1 | 0.42 | 1:2 |
| | | 0.4 | 1 | 0.37 | 1:2.5 |
| | | 0.3 | 1 | 0.32 | 1:3.33 |
| | | 0.2 | 1 | 0.27 | 1:5 |
| | | 0.16 | 1 | 0.25 | 1:6.25 |
| | | 0.09 | 1 | 0.21 | 1:11.1 |
| | | 0.9 | 2 | 0.78 | 1:2.22 |
| | | 0.7 | 2 | 0.68 | 1:2.86 |
| | | 0.5 | 2 | 0.58 | 1:4 |
| | | 0.4 | 2 | 0.53 | 1:5 |
| | | 0.3 | 2 | 0.48 | 1:6.67 |
| | | 0.2 | 2 | 0.43 | 1:10 |
| | | 0.16 | 2 | 0.41 | 1:12.5 |
| | | 0.09 | 2 | 0.38 | 1:22.22 |
| | | 0.5 | 4 | 0.92 | 1:8 |
| | | 0.4 | 4 | 0.87 | 1:10 |
| | | 0.3 | 4 | 0.82 | 1:13.3 |
| | | 0.2 | 4 | 0.77 | 1:20 |
| | | 0.16 | 4 | 0.75 | 1:25 |
| | | 0.09 | 4 | 0.71 | 1:44.4 |
| | | 0.07 | 4 | 0.7 | 1:57.1 |
| | | 0.05 | 4 | 0.69 | 1:80 |
| | | 0.04 | 4 | 0.69 | 1:100 |
| *A. niger* ATCC # 16404 | 3 days | 26 | — | — | |
| | | — | 6 | — | |
| | | 21 | 0.25 | 0.85 | 1:0.012 |
| | | 21 | 0.5 | 0.89 | 1:0.024 |
| | | 17 | 0.5 | 0.74 | 1:0.029 |
| | | 21 | 1 | 0.97 | 1:0.048 |
| | | 17 | 1 | 0.82 | 1:0.059 |
| | | 12 | 1 | 0.63 | 1:0.083 |
| | | 17 | 2 | 0.99 | 1:0.118 |
| | | 12 | 2 | 0.79 | 1:0.167 |
| | | 8 | 2 | 0.64 | 1:0.25 |
| | | 4.4 | 2 | 0.5 | 1:0.45 |
| | | 8 | 4 | 0.97 | 1:0.5 |
| | | 4.4 | 4 | 0.84 | 1:0.91 |
| | | 3.5 | 4 | 0.8 | 1:1.14 |
| | 7 days | 35 | — | — | |
| | | — | 6 | — | |
| | | 26 | 0.5 | 0.83 | 1:0.019 |
| | | 21 | 0.5 | 0.68 | 1:0.024 |
| | | 26 | 1 | 0.91 | 1:0.038 |
| | | 21 | 1 | 0.77 | 1:0.047 |
| | | 17 | 1 | 0.65 | 1:0.059 |
| | | 21 | 2 | 0.93 | 1:0.095 |
| | | 17 | 2 | 0.82 | 1:0.118 |
| | | 12 | 2 | 0.68 | 1:0.167 |
| | | 8 | 2 | 0.56 | 1:0.25 |
| | | 8 | 4 | 0.9 | 1:0.5 |

Ca = as Free Cl$_2$ Component A (Sodium hypochlorite)
Cb = Component B (Ag-polymer formulation)

TABLE 11

| Test Organisms | Contact Time | Ca | Cb | S.I. | Ca:Cb |
|---|---|---|---|---|---|
| *P. aeruginosa* ATCC # 15442 | 24 hour | 16 | — | — | |
| | | — | 0.06 | — | |
| | | 13 | 0.008 | 0.95 | 1:0.000615 |
| | 48 hour | 20 | — | — | |
| | | — | 0.06 | — | |
| | | 16 | 0.002 | 0.83 | 1:0.000125 |
| | | 16 | 0.004 | 0.87 | 1:0.00025 |
| | | 16 | 0.008 | 0.93 | 1:0.0005 |
| *S. aureus* ATCC # 6538 | 24 hour | 13 | — | — | |
| | | — | 0.06 | — | |
| | | 9 | 0.001 | 0.71 | 1:0.00011 |
| | | 6 | 0.001 | 0.48 | 1:0.00017 |
| | | 9 | 0.002 | 0.73 | 1:0.00022 |
| | | 6 | 0.002 | 0.49 | 1:0.00033 |
| | | 9 | 0.004 | 0.76 | 1:0.00044 |
| | | 6 | 0.004 | 0.53 | 1:0.00067 |
| | | 3 | 0.004 | 0.3 | 1:0.0013 |
| | | 9 | 0.008 | 0.83 | 1:0.00089 |
| | | 6 | 0.008 | 0.59 | 1:0.0013 |
| | | 3 | 0.008 | 0.36 | 1:0.0027 |
| | | 9 | 0.016 | 0.96 | 1:0.0018 |
| | | 6 | 0.016 | 0.73 | 1:0.0027 |
| | | 3 | 0.016 | 0.5 | 1:0.0053 |
| | | 6 | 0.03 | 0.96 | 1:0.005 |
| | | 3 | 0.03 | 0.73 | 1:0.01 |
| | | 2.6 | 0.03 | 0.7 | 1:0.012 |
| | 48 hour | 20 | — | — | |
| | | — | 0.06 | — | |
| | | 16 | 0.001 | 0.82 | 1:0.00006 |
| | | 13 | 0.001 | 0.67 | 1:0.00008 |
| | | 16 | 0.002 | 0.83 | 1:0.00013 |
| | | 13 | 0.002 | 0.68 | 1:0.00015 |
| | | 16 | 0.004 | 0.87 | 1:0.00025 |
| | | 13 | 0.004 | 0.72 | 1:0.00031 |
| | | 9 | 0.004 | 0.52 | 1:0.00044 |
| | | 6 | 0.004 | 0.37 | 1:0.00067 |
| | | 16 | 0.008 | 0.93 | 1:0.0005 |
| | | 13 | 0.008 | 0.78 | 1:0.0006 |
| | | 9 | 0.008 | 0.58 | 1:0.00089 |
| | | 6 | 0.008 | 0.43 | 1:0.00133 |
| | | 3 | 0.008 | 0.28 | 1:0.0027 |
| | | 13 | 0.016 | 0.92 | 1:0.0012 |
| | | 9 | 0.016 | 0.72 | 1:0.0018 |
| | | 6 | 0.016 | 0.57 | 1:0.0027 |
| | | 3 | 0.016 | 0.42 | 1:0.00533 |
| | | 9 | 0.03 | 0.95 | 1:0.0033 |
| | | 6 | 0.03 | 0.8 | 1:0.005 |
| | | 3 | 0.03 | 0.65 | 1:0.01 |
| *C. albicans* ATCC # 10231 | 24 hour | 88 | — | — | |
| | | — | 6 | — | |
| | | 65 | 0.25 | 0.78 | 1:0.0038 |
| | | 53 | 0.25 | 0.64 | 1:0.0047 |
| | | 65 | 0.5 | 0.82 | 1:0.0077 |
| | | 53 | 0.5 | 0.69 | 1:0.0094 |
| | | 65 | 1 | 0.91 | 1:0.0154 |
| | | 53 | 1 | 0.77 | 1:0.0189 |
| | | 43 | 1 | 0.66 | 1:0.0232 |
| | | 53 | 2 | 0.94 | 1:0.038 |
| | | 43 | 2 | 0.82 | 1:0.047 |
| | 48 hour | 88 | — | — | |
| | | — | 6 | — | |
| | | 65 | 0.25 | 0.78 | 1:0.0038 |
| | | 65 | 0.5 | 0.82 | 1:0.0077 |
| | | 53 | 0.5 | 0.69 | 1:0.0094 |

TABLE 11-continued

| Test Organisms | Contact Time | Ca | Cb | S.I. | Ca:Cb |
|---|---|---|---|---|---|
| | | 65 | 1 | 0.91 | 1:0.015 |
| | | 53 | 1 | 0.77 | 1:0.019 |
| | | 43 | 1 | 0.66 | 1:0.023 |
| | | 53 | 2 | 0.94 | 1:0.038 |
| | | 43 | 2 | 0.82 | 1:0.047 |
| A. niger ATCC # 16404 | 3 days | 525 | — | — | |
| | | — | 6 | — | |
| | | 425 | 1 | 0.98 | 1:0.0024 |
| | 7 days | 650 | — | — | |
| | | — | 6 | — | |
| | | 525 | 1 | 0.97 | 1:0.0019 |

Ca = Component A - (Glutaraldehyde)
Cb = Component B - (Ag-polymer formulation)

TABLE 12

| Test Organisms | Contact Time | Ca | Cb | S.I. | Ca:Cb |
|---|---|---|---|---|---|
| P. aeruginosa ATCC # 15442 | 24 hour | 30 | — | — | |
| | | — | 0.06 | — | |
| | | 20 | 0.008 | 0.8 | 1:0.0004 |
| | | 20 | 0.016 | 0.93 | 1:0.0008 |
| | 48 hour | 43 | — | — | |
| | | — | 0.06 | — | |
| | | 30 | 0.008 | 0.83 | 1:0.00027 |
| | | 30 | 0.016 | 0.96 | 1:0.00053 |
| | | 20 | 0.03 | 0.97 | 1:0.0015 |
| S. aureus ATCC # 6538 | 24 hour | 9 | — | — | |
| | | — | 0.06 | — | |
| | | 7 | 0.002 | 0.81 | 1:0.00029 |
| | | 7 | 0.004 | 0.84 | 1:0.00057 |
| | | 7 | 0.008 | 0.91 | 1:0.0011 |
| | | 5 | 0.008 | 0.69 | 1:0.0016 |
| | | 5 | 0.016 | 0.82 | 1:0.0032 |
| | | 4 | 0.03 | 0.94 | 1:0.0075 |
| | | 3 | 0.03 | 0.83 | 1:0.01 |
| | 48 hour | 11 | — | — | |
| | | — | 0.06 | — | |
| | | 9 | 0.001 | 0.83 | 1:0.00011 |
| | | 9 | 0.002 | 0.85 | 1:0.00022 |
| | | 9 | 0.004 | 0.88 | 1:0.00044 |
| | | 9 | 0.008 | 0.95 | 1:0.00089 |
| | | 7 | 0.016 | 0.9 | 1:0.0023 |
| A. niger ATCC # 16404 | 3 days | 9 | — | — | |
| | | — | 6 | — | |
| | | 7 | 1 | 0.94 | 1:0.143 |
| | 7 days | 30 | — | — | |
| | | — | 6 | — | |
| | | 20 | 0.5 | 0.75 | 1:0.025 |
| | | 20 | 1 | 0.83 | 1:0.05 |
| | | 11 | 2 | 0.7 | 1:0.18 |
| | | 9 | 2 | 0.63 | 1:0.22 |
| | | 9 | 4 | 0.97 | 1:0.44 |
| | | 7 | 4 | 0.9 | 1:0.57 |

Ca = Component A - 5-Chloro-2-(2,4-dichlorophenoxy)phenol
Cb = Component B (Ag-polymer formulation)

TABLE 13

| Test Organisms | Contact Time | Ca | Cb | S.I. | Ca:Cb |
|---|---|---|---|---|---|
| P. aeruginosa ATCC # 15442 | 24 hour | 1050 | — | | |
| | | — | 0.06 | | |
| | | 850 | 0.002 | 0.84 | 1:0.000002 |
| | | 850 | 0.004 | 0.88 | 1:0.000005 |
| | | 850 | 0.008 | 0.94 | 1:0.000009 |
| | 48 hour | 1300 | — | | |
| | | — | 0.06 | | |
| | | 1050 | 0.002 | 0.84 | 1:0.000002 |

TABLE 13-continued

| Test Organisms | Contact Time | Ca | Cb | S.I. | Ca:Cb |
|---|---|---|---|---|---|
| | | 1050 | 0.004 | 0.87 | 1:0.000004 |
| | | 1050 | 0.008 | 0.94 | 1:0.000008 |
| S. aureus ATCC # 6538 | 24 hour | 14 | — | — | |
| | | — | 0.06 | — | |
| | | 8 | 0.001 | 0.59 | 1:0.00013 |
| | | 8 | 0.002 | 0.6 | 1:0.00025 |
| | | 8 | 0.004 | 0.64 | 1:0.0005 |
| | | 6 | 0.004 | 0.5 | 1:0.0007 |
| | | 8 | 0.008 | 0.7 | 1:0.001 |
| | | 6 | 0.008 | 0.56 | 1:0.0013 |
| | | 8 | 0.016 | 0.84 | 1:0.002 |
| | | 6 | 0.016 | 0.7 | 1:0.0027 |
| | | 6 | 0.03 | 0.93 | 1:0.005 |
| | | 5 | 0.03 | 0.86 | 1:0.006 |
| | | 4 | 0.03 | 0.79 | 1:0.0075 |
| | | 3 | 0.03 | 0.71 | 1:0.01 |
| | 48 hour | 14 | — | — | |
| | | — | 0.06 | — | |
| | | 8 | 0.001 | 0.59 | 1:0.00013 |
| | | 8 | 0.002 | 0.6 | 1:0.00025 |
| | | 8 | 0.004 | 0.64 | 1:0.0005 |
| | | 6 | 0.004 | 0.5 | 1:0.0007 |
| | | 8 | 0.008 | 0.7 | 1:0.001 |
| | | 6 | 0.008 | 0.56 | 1:0.00131 |
| | | 8 | 0.016 | 0.84 | 1:0.002 |
| | | 6 | 0.016 | 0.7 | 1:0.0027 |
| | | 6 | 0.03 | 0.93 | 1:0.005 |
| | | 4 | 0.03 | 0.79 | 1:0.0075 |
| A. niger ATCC # 16404 | 3 days | 0.4 | — | — | |
| | | — | 6 | — | |
| | | 0.3 | 1 | 0.92 | 1:3.33 |
| | | 0.2 | 1 | 0.67 | 1:5 |
| | | 0.2 | 2 | 0.83 | 1:10 |
| | | 0.1 | 4 | 0.92 | 1:40 |
| | | 0.08 | 4 | 0.87 | 1:50 |
| | | 0.06 | 4 | 0.82 | 1:66.7 |
| | | 0.05 | 4 | 0.79 | 1:80 |
| | 7 days | 0.8 | — | — | |
| | | — | 6 | — | |
| | | 0.6 | 1 | 0.92 | 1:1.67 |
| | | 0.5 | 1 | 0.79 | 1:2 |
| | | 0.4 | 1 | 0.67 | 1:2.5 |
| | | 0.3 | 1 | 0.54 | 1:3.3 |
| | | 0.5 | 2 | 0.96 | 1:4 |
| | | 0.4 | 2 | 0.83 | 1:5 |
| | | 0.3 | 2 | 0.71 | 1:6.7 |
| | | 0.2 | 2 | 0.58 | 1:10 |
| | | 0.1 | 2 | 0.46 | 1:20 |
| | | 0.2 | 4 | 0.92 | 1:20 |
| | | 0.1 | 4 | 0.79 | 1:40 |
| | | 0.08 | 4 | 0.77 | 1:50 |
| | | 0.06 | 4 | 0.74 | 1:66.7 |
| | | 0.05 | 4 | 0.73 | 1:80 |

Ca = Component A - 3-Iodo-2-propynyl butylcarbamate
Cb = Component B (Ag-polymer formulation)

The invention claimed is:
1. A synergistic microbicidal composition; said composition comprising:
    (a) a silver-containing copolymer comprising polymerized units of a monomer X and a monomer Y;
wherein the copolymer comprises 5 wt % to 11.5 wt % silver, based on total copolymer weight; and wherein monomer X is N-vinylimidazole and monomer Y comprises at least one $C_2$-$C_8$ alkyl (meth)acrylate; and
    (b) $C_{12}$-$C_{16}$ alkyl dimethylbenzylammonium chloride, $C_9$-$C_{15}$ alkyltolylmethyl trimethylammonium chloride, hydrogen peroxide, or a combination thereof;
wherein a weight ratio of silver to $C_{12}$-$C_{16}$ alkyl dimethylbenzylammonium chloride is from 1:19.6 to 1:980, a weight ratio of silver to $C_9$-$C_{15}$ alkyltolylmethyltrimethylammonium chloride is from 1:39.2 to 1:1152 and a weight ratio of hydrogen peroxide to silver is from 1:0.000005 to 1:0.000121.

2. The composition of claim 1, wherein the copolymer comprises 6.5 wt % to 8.5 wt % silver, based on total weight of copolymer and silver.

3. The composition of claim 2, wherein the copolymer comprises 35 to 55 wt % of units derived from monomer X and 45 to 65 wt % of units derived from monomer Y.

4. The composition of claim 3, wherein monomer Y comprises n-butyl acrylate and acrylic acid.

5. The composition of claim 1 comprising the silver-containing copolymer and $C_{12}$-$C_{16}$ alkyl dimethylbenzylammonium chloride, $C_9$-$C_{15}$ alkyltolylmethyl trimethylammonium chloride or combinations thereof.

6. The composition of claim 5, wherein the copolymer comprises 6.5 wt % to 8.5 wt % silver, based on total weight of copolymer and silver; and wherein the copolymer comprises 35 to 55 wt % of units derived from monomer X and 45 to 65 wt % of units derived from monomer Y.

7. The composition of claim 1 comprising the silver-containing copolymer and hydrogen peroxide, wherein the copolymer comprises 6.5 wt % to 8.5 wt % silver, based on total weight of copolymer and silver; and wherein the copolymer comprises 35 to 55 wt % of units derived from monomer X and 45 to 65 wt % of units derived from monomer Y.

* * * * *